United States Patent [19]

Marlin et al.

[11] Patent Number: 5,645,827
[45] Date of Patent: *Jul. 8, 1997

[54] MUCO-ADHESIVE POLYMERS

[75] Inventors: Lawrence Marlin, Bridgewater, N.J.; Ronald Kenichi Yamamoto, San Francisco, Calif.

[73] Assignee: Union Carbide Chemicals & Plastics Technology Corporation, Danbury, Conn.

[*] Notice: The term of this patent shall not extend beyond the expiration date of Pat. No. 5,358,706.

[21] Appl. No.: 375,498

[22] Filed: Jan. 19, 1995

Related U.S. Application Data

[63] Continuation-in-part of Ser. No. 329,104, Oct. 25, 1994, abandoned, which is a continuation of Ser. No. 954,753, Sep. 30, 1992, Pat. No. 5,358,706.

[51] Int. Cl.$^6$ .......................... A61K 31/74; A61K 47/36
[52] U.S. Cl. .......... 424/78.04; 424/434; 424/435; 514/777; 514/912; 514/913; 514/914; 514/915
[58] Field of Search .............. 424/434, 78.04, 424/427, 78.05, 78.06, 78.07, 435; 604/890.1; 514/777, 912, 913, 914, 915

[56] References Cited

U.S. PATENT DOCUMENTS

| | | | |
|---|---|---|---|
| 3,472,840 | 10/1969 | Stone et al. | 260/231 |
| 3,947,573 | 3/1976 | Rankin | 424/80 |
| 3,980,769 | 9/1976 | Ghilardi et al. | 394/346 |
| 4,303,676 | 12/1981 | Balazs | 424/359 |
| 4,321,261 | 3/1982 | Ellis et al. | 424/180 |
| 4,362,697 | 12/1982 | Tabb et al. | 422/56 |
| 4,617,186 | 10/1986 | Schafer et al. | 424/78 |
| 4,663,159 | 5/1987 | Brode, II et al. | 424/70 |
| 4,767,463 | 8/1988 | Brode et al. | 424/78.04 |
| 4,913,743 | 4/1990 | Brode et al. | 106/162 |
| 5,106,615 | 4/1992 | Dikstein | 424/78.04 |
| 5,171,526 | 12/1992 | Wong et al. | 422/28 |
| 5,407,919 | 4/1995 | Brode et al. | 424/70.1 |

FOREIGN PATENT DOCUMENTS

| | | |
|---|---|---|
| 9102538 | 3/1991 | European Pat. Off. |
| 3440352 | 5/1986 | Germany |

Primary Examiner—Carlos Azpuru
Attorney, Agent, or Firm—W. K. Volles

[57] ABSTRACT

Compositions comprising cationic polysaccharide polymers and anionic therapeutic agents which can have enhanced substantivity to mucosal surfaces are disclosed. These compositions are well suited, for example, for the delivery of anionic ophthalmic pharmaceuticals because they can provide clear solution in addition to substantivity.

17 Claims, 2 Drawing Sheets

MUCO-ADHESIVE POLYMERS

This application is a continuation-in-part of application Ser. No. 08/329,104 filed Oct. 25, 1994, now abandoned, which is a continuation of application Ser. No. 07/954,753, filed Sep. 30, 1992, now U.S. Pat. No. 5,358,706.

FIELD OF THE INVENTION

The present invention relates to the use of cationic polymers having bioadhesive properties. More specifically, this invention relates to the use of cationic polysaccharide polymers to treat infirmities of mucosal surfaces.

BACKGROUND OF THE INVENTION

The delivery of therapeutic substances to mucosal surfaces has inherent difficulties due to the moist surface. This is particularly true for the mucosal surface of the eye where the washing action of the tear film removes much of the therapeutic substance. Estimates of the portion of a drug delivered by means of a topical drop range from 1 to 10% of the drug content. The remaining portion of the drug which does not penetrate or adhere to the eye is removed by tears through the lacrimal ducts where systemic absorption occurs through contact with nasal and gastro-intestinal surfaces.

A common ophthalmic problem, particularly with older people, is the condition commonly known as "dry eye" or dyslacrima. As people age, the tear ducts in the eye produce less moisture. Consequently, the eye becomes dry, inflamed and irritated.

There is a need for a method for treating mucosal surfaces such as, for example, the eye, in order to retain an active agent for a longer period of time.

SUMMARY OF THE INVENTION

This invention pertains to topical substantive delivery systems for mucosal tissues comprising a clear aqueous solution of a cationic polysaccharide and an anionic therapeutic active ingredient. The present invention is particularly well suited to deliver anionic therapeutic agents, such as, for example, hyaluronic acid or its salt, to the surface of the eye.

Figure 1:
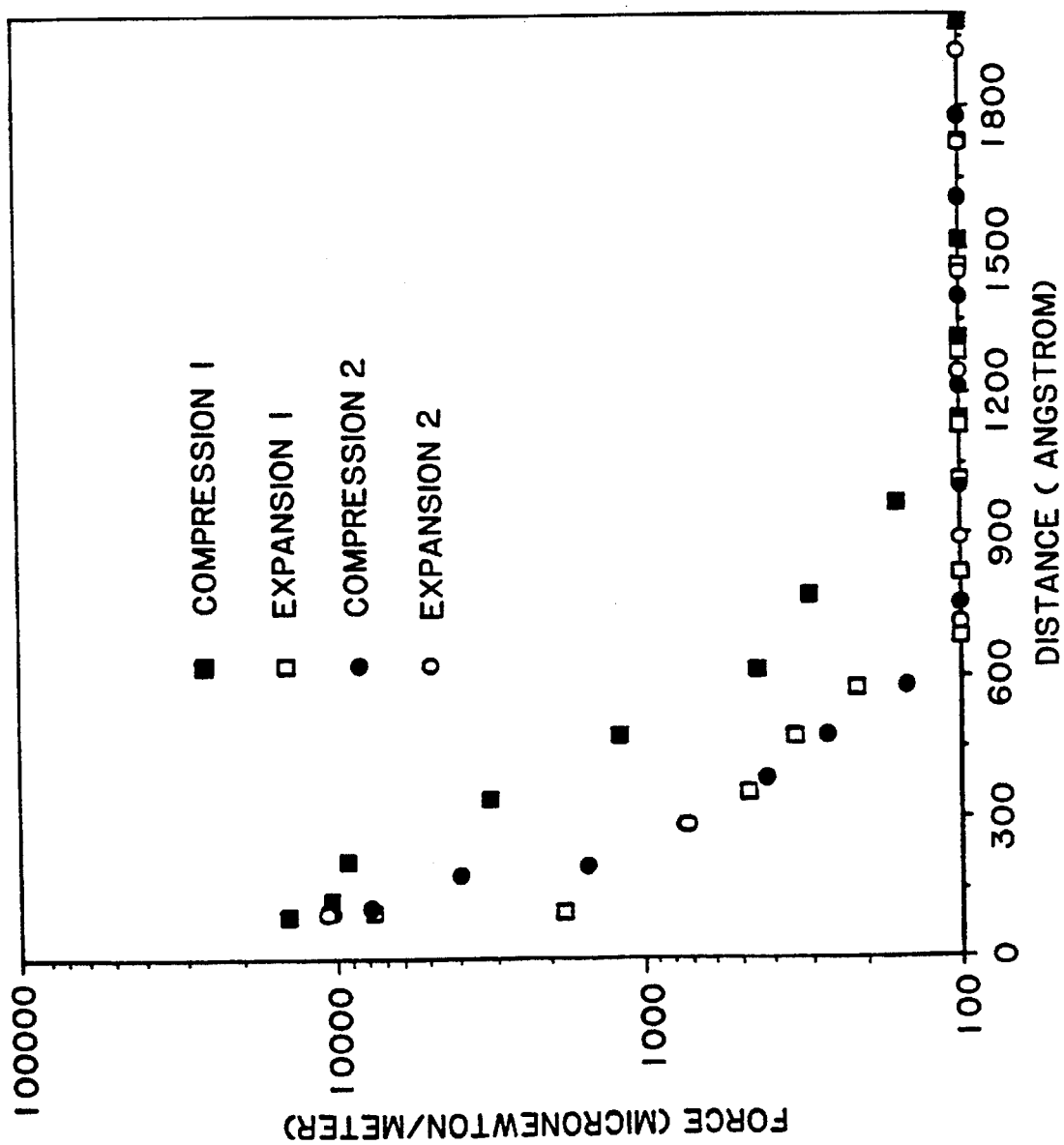
FIG. 1 is a force versus distance profile of a 1000 parts per million aqueous UCARE® Polymer JR 400 solution squeezed between two mica plates.

Both FIGS. 1 and 2 relate to Example 2 which is further described in the specification herein below.

DETAILED DESCRIPTION OF THE INVENTION

The present invention provides methods for binding cationic polymers to mucosal surfaces. The cationic polymers of the present invention have been found to be substantive to the mucosal surfaces and can topically deliver various therapeutic agents to the mucosal surface.

Cationic polysaccharide polymers and therapeutic agent combinations are provided which form highly substantive films. Cationic polymer delivery systems have been previously disclosed and found to be substantive to keratinous material in U.S. Pat. Nos. 4,767,463 and 4,913,743. Keratin is a scleroprotein which is the principal constituent of skin, hair, nails and the organic matrix of the enamel of the teeth. The mucosal surfaces of the body are not comprised of keratin.

Mucosal surfaces in the body include but are not limited to the outer covering or globe of the eye, the inside lining of the mouth, nose and vagina. These surfaces are generally soft, moist tissue. For example, the globe or outer covering of the eye is comprised of non-keratinized epithelium (Bloom, W. and Fawcett, D. W., *A TEXTBOOK OF HISTOLOGY*, 10th Ed., W. B. Saunders Co., Philadelphia 1975). The surface of the eye is continuously coated with water from the tear ducts which frequently washes material away from the outer coating of the eye. It has been surprisingly discovered that the cationic polysaccharide polymers of the present invention are substantive to mucosal surfaces such as the eye while being non-irritating.

The cationic polysaccharide polymers which are useful in the present invention include, but are not limited to: the starch and cellulose families; pectin; chitin; chitosan; guar; and the like.

Preferably, the cationic polysaccharides are substituted with greater than about 0.1, preferably from about 0.2 to 1.0, mole per mole of polysaccharide of a quaternary nitrogen compound having hydrocarbon substituents with from 1 to about 4 carbon atoms per substituent. As used herein, the term "substituent" is made with reference to substituents other than the substituent which is connected to the polysaccharides, although it is typical for the connecting substituent to also have up to about 4 carbon atoms. Preferably, the connecting substituent comprises an alkoxyalkyl radical with a least 2 carbon atoms separating the oxygen atom from the nitrogen atom. Preferably, the other substituents will be either methyl or ethyl and the total number of carbon atoms in such other substituents will be from about 3 to 6, more preferably about 4. A preferred regent suitable for substitution onto the polysaccharide is 2,3 epoxypropyl trimethyl ammonium chloride. Preferably, the type of quaternary substitutent and substitution level is effective to provide substantivity to the mucosal surface and a clear solution, even when the solution contains isotonic salt, e.g., 9 grams of sodium chloride per liter of water. Further details concerning the preparation of suitable cationic polysaccharides is known to those skilled in the art.

The molecular weight of the cationic polysaccharides suitable for use in accordance with the present invention typically ranges from about 10,000 to 1,00,000 grams per gram mole and preferably ranges from about 20,000 to 500,000 grams per gram mole. As used herein, the term "molecular weight" means weight average molecular weight. Methods for determining weight average molecular weight of polysaccharides are known to those skilled in the art. One preferred method for determining molecular weight is low angle laser light scattering. The viscosity of the cationic polysaccharides typically ranges from about 5 to 10,000 centipoise, preferably from about 10 to 2,000 centipoise. Unless otherwise indicated, as used herein the term "viscosity" refers to the viscosity of a 2.0 weight percent aqueous solution of the polymer measured at 25° C. with a Brookfield viscometer. Such viscosity measuring techniques are known in the art.

Preferred cationic polysaccharides include, but are not limited to, water soluble polymers which may be selected from he following: quaternary nitrogen-containing cellulose ethers such as UCARE® Polymers JR-125, JR-400, JR-30M, LR-400, LR-30M and SR-10 provided by Union Carbide Corporation, Danbury, Conn. These polymers have a backbone. As a result of the presence of the positively charged groups imparting cationic character to the polymer, these polymers exhibit increased substantivity to the mucosal surface.

The essential substituent groups on the anhydroglucose backbone are ether groups comprising a quaternary-nitrogen radical. Additional ether groups which do not contain a quaternary-nitrogen radical may, and preferably will, also be present. The cellulose ethers are produced by etherification of a cellulosic material; the reactions involved in their preparation being the introduction of an ether group comprising a quaternary-nitrogen radical.

The cellulose ethers of this invention are polymers of the structural formula:

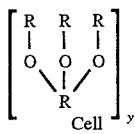

where $^R$Cell is the residue of an anhydroglucose unit ($C_6H_{10}O_5$), the R's may be the same or different and each R individually represents a substituent group of the formula given herein below, and y represents the degree of polymerization and is an integer having a value of from about 50 to about 20,000, or more, and preferably from about 200 to about 5,000.

In the above structural formula each R individually represents a substituent group of the general formula:

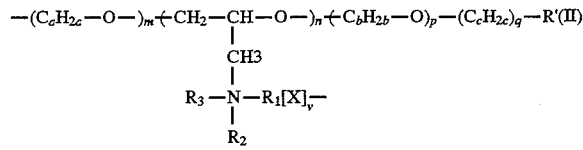

wherein:
a is an integer having a value of from 2 to 3;
b is an integer having a value of from 2 to 3;
c is an integer having a value of from 1 to 3;
m is an integer having a value of from zero to 10;
n is an integer having a value of from zero to 3;
p is an integer having a value of from zero to 10;
q is an integer having a value of from zero to 1;
R' is a member selected from the group consisting of

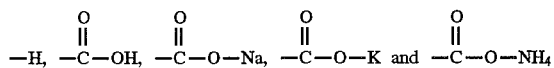

with the proviso that when q is zero the R' is —H;
$R_1$, $R_2$ and $R_3$, taken individually, represent a member selected from the group consisting of alkyl and alkoxyalkyl radicals where each of $R_1$, $R_2$ and $R_3$ can contain up to 4 carbon atoms, with the provision that when said member is an alkoxyalkyl radical there are at least 2 carbon atoms separating the oxygen atom from the nitrogen atom, and with the further proviso that the total number of carbon atoms in radicals represented by $R_1$, $R_2$ and $R_3$ is from 3 to 6.

X is an anion such as chloride, bromide, iodide, sulfate, methylsulfate, sulfonate, nitrate, phosphate, acetate, etc., and V is an integer which is equal to the valence of X.

The average value of n per anhydroglucose unit is from about 0.01 to about 1 and preferably from about 0.1 to about 0.5.

The average value of m+n+p+q per anhydroglucose unit is from about 0.01 to about 7.0, more preferably from about 0.1 to about 5.0, and most preferably from bout 0.8 to about 3.0.

Illustrative of the numerous possible pendant groups on the anhydroglucose chain in accordance with the above generic description are the following:

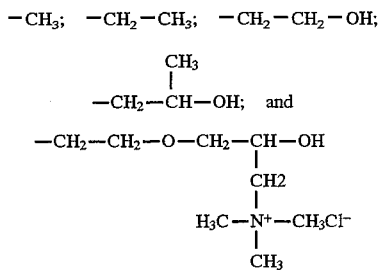

The number of quaternary nitrogen atoms per substituent, defined by n in Formula II, is greater than or equal to 0, i.e., n is an integer greater than or equal to 0.

Anionic therapeutic agents which can be used in conjunction with the cationic polymers of the present invention include any anionic compound which can enhance the substantivity of the cationic polysaccharide to the mucosal surface. Such compounds may be, for example, anti-inflammatory agents, anti-infection agents, glaucoma agents, imaging agents, wound healing agents, dry eye agents and mixtures thereof. Therapeutic agents, as used herein, are broadly defined to be ingredients which treat, diagnosis or prevent diseases or disorders of the body. Therapeutic agents, include humectants and/or lubricants which could alleviate conditions such as dry eye or ulcerations associated with contact lens wear or pharmaceuticals which effect bodily functions. Dry eye agents include glycosaminoglycans such as hyaluronic acid or salts thereof, and other dry eye agents such as chondroitin sulphate, and the like. Illustrative anti-inflammatory agents include prostoglandins and derivatives; salicyclic acid; proprionic acid; fenemates including anthranilic acid, derivatives and salts thereof, and cromolyn. Anti-infective agents include beta lactam antibiotics such as penicillins and cephalosporin. Glaucoma agents include carbonic anhydrase inhibitors and the like; imaging agents include fluorescein and derivatives and rose bengal and the like: and wound healing agents including peptide growth factors such as epidermal growth factor and the like.

Gylcosaminoglycans are anionic active ingredients that can be used with particular advantage with the cationic polymers of the present invention. Glycosaminoglycans are well known, naturally occurring, polysaccharides containing disaccharide repeating units of hezosamine and hexose or hexuronic acid and may contain sulfate groups.

Representative glycosaminoglycans include, but are not limited to: hyaluronan, hyaluronic acid or derivatives thereof such as hylan; heparin; heparan; chondroitin; keratan; and sulfates of such materials. A particularly preferred glycosaminoglycan is hyaluronan, and derivatives thereof, which contain repeating disaccharide structure of D-glucuronic acid and 2-acetamido- 2-desoxy-D-glucose joined by alternating β1→3 glucuronidic and β1→4 glucosaminidic bonds. Representative hyaluronan and derivatives thereof which may be provided include, but are not limited to: BIOMATRIX® hyaluronan provided by Biomatrix, Inc., such as described in U.S. Pat. No. 4,303,676 (Balazs), HYLADERM® hylan provided by Biomatrix, Inc., such as described in U.S. Pat. No. 4,713,448 (Balazs, et al.); and substantially pure hyaluronan such as described in U.S. Pat. No. 4,141,973 (Balazs).

Preferably, the anionic therapeutic agent will comprise carboxylic acid groups, sulfate groups, salts or derivatives thereof in its structure.

The ratio of the cationic polysaccharide polymer to the therapeutic agent may vary widely. In a preferred embodiment, after the anionic therapeutic agent is added to the cationic polysaccharide polymer, sufficient cationic charge remains on the polysaccharide polymer to bind the polymer to the mucosal surface, i.e. the complex of the cationic polysaccharide polymer and the anionic therapeutic agent will have an effective number of free cationic groups to provide substantivity to the mucosal surface. Those with ordinary skill in the art will appreciate that manipulation of the cationic substitution of the polymer and/or the level of polymer employed can be used in determining the effective amount.

In a broad sense, the relative proportion of cationic polymer to therapeutic agent is not narrowly critical. The relative weight ratio of cationic polymer to therapeutic agent will preferably range from 1:1 to about 200:1, more preferably from about 2:1 to about 100:1 and most preferably from about 10:1 to about 50:1.

Typically, the amount of therapeutic agent is at least about 0.0001 weight percent, preferably from about 0.0005 weight percent to about 2.0 weight percent and more preferably from about 0.001 weight percent to about 1.0 weight percent and most preferably from about 0.001 weight percent to less than about 0.6 weight percent based on the total composition. Preferably, the amount of anionic therapeutic agent will be effective to enhance the substantivity between the anionic therapeutic agent and the cationic polysaccharide and retain a clear solution.

The specific amount of cationic polysaccharide polymer provided may also vary widely. In a preferred embodiment the cationic polymer is provided in an amount sufficient to be substantive to the mucosal surface. Typically, the amount of cationic polymer is at least about 0.0005 weight percent, preferably from about 0.0025 weight percent to about 20.0 weight percent and most preferably from about 0.005 weight percent to about 10 weight percent of the total composition.

The cationic polysaccharide polymer solutions of this invention are employed to deliver anionic therapeutic ingredients. Without wishing to being bound by any theory, it is believed that electrostatic forces bind the anionic therapeutic agents to the cationic polymer. Thus, when the cationic polysaccharide polymer is substantive to the mucosal surface, the anionic therapeutic agent is also delivered to the mucosal surface. The present invention is also capable of delivery a therapeutic agent which is chemically reacted to form a covalent bond to the cationic polysaccharide as in the case of a salt.

Substantivity of the anionic therapeutic agent and cationic polysaccharide polymer combination is characterized by an increase of the cationic polysaccharide polymer on the mucosal surface.

Substantivity can be measured through the use of an ocular fluorimeter. The cationic polysaccharide polymer is fluorescently tagged by reaction with fluorescein generally based on the procedure of De Balder and Granath for labeling dextrans; *Carbohydrate Research*, 30 (1973) 375–378.

Through selection and optimization of the various related structural parameters influencing viscosification, cationic polysaccharide polymers of this invention can be produced which provide a desired level of viscosity, within a potentially wide range of values. Aqueous solutions containing 0.5 weight percent concentrations cationic polysaccharide polymers of this invention will usually have a Brookfield viscosity at 25° C. of less than 50 centipoise (cps), and preferably from about 5 to about 30 cps.

The cationic polymer and therapeutic agents of this invention are typically provided to the mucosal surface in an aqueous solution typically neutral buffered and isotonic, similar to artificial tear solutions. Typically, the range in the level of isotonic salts employed is up to about 0.9 parts by weight for inorganic salts and up to about 6.0 parts by weight for organic substances. Illustrative inorganic . isotonicizers include sodium chloride, boric acid and borax, while natural substance isotonicizers are generally sugars such as mannitol and sorbital. The pH of these isotonicized solutions can vary widely from 3 to 9. If the cationic polymer and anionic therapeutic agent are to be placed in the eye, the pH of the solution should be as close as possible to neutral and should always be within the range of pH 6–8.

Contrary to the suggestion of the prior art that salts can not be employed in conjunction with an anionic agent and a cationic polymer, it has been found that stable, clear solutions can be formed. Clarity as used herein is defined to mean that the solution is substantially particulate free and does not form a precipitate, coacervate or is opalescent.

A preferred method, in accordance with the present invention, for delivery of an anionic therapeutic agent to a mucosal surface, e.g., the eyes, comprises providing a aqueous solution to the mucosal surface, said aqueous solution comprising:

(a) water;
(b) a cationic polysaccharide polymer with a cationic substitution of greater than about 0.2 which is substantive to the mucosal surface; and
(c) an anionic therapeutic agent;

wherein the anionic therapeutic agent is selected from the group consisting of hyaluronan, hyaluronic acid, hyaluronan derivatives, penicillins, salicylic acid, anthranilic acid, derivatives and salts thereof, the anionic therapeutic agent is electrostatically bonded to the cationic polysaccharide and the solution is clear.

The aqueous solutions of the present invention can be provided topically to the mucosal surface as a gel, lotion or cream. In a preferred embodiment, drops are used to deliver therapeutic agents to the eye.

Other optional ingredients may also be employed including but not limited to thickeners, surfactants, pH adjusters and preservatives. The amount of optional ingredients contained in the combinations of this invention is not critical but will vary depending upon the particular ingredient, composition and desired use level and may be any effective amount for achieving the desired property provided by such ingredients, following procedures known to those in the art.

Whereas the exact scope of the instant invention is set forth in the appended claims, the following specific examples illustrate certain aspects of the present invention and, more particularly, point out methods of evaluating the same. However, the examples are set forth for illustration only and are not to be construed as limitations on the present invention except as set forth in the appended claims. All parts and percentages are by weight unless otherwise specified.

DEFINITIONS

The following designations used in the Examples and elsewhere herein have the following meaning:

JR—UCARE® Polymer JR 400, a cationic cellulosic polymer (N,N,N-trimethyl ammonium chloride hydroxyethyl cellulose) with a molecular weight of approximately 500,000 available from Union Carbide Corporation, Danbury, Conn.

LR—UCARE® Polymer LR, a cationic cellulosic polymer (N,N,N-trimethyl ammonium chloride hydroxyethyl cellulose) with a molecular weight of approximately 500,000 available from Union Carbide Corporation, Danbury, Conn.

HEC—hydroxyethyl cellulose, cellosize HEC WP-300, available from Union Carbide Corporation, Danbury, Conn. with a molecular weight of approximately 500,000.

EXAMPLE 1

Three aqueous 0.5 weight percent polymer solutions were prepared using JR, LR and HEC. The solutions were dialyzed to remove excess salt and low molecular weight contaminants. The solutions were made pH neutral, sterile and isotonic prior to the polymer being fluoroscein tagged.

A 20 microliter drop of the respective solutions was placed in a subject's eye. The presence of the fluorescently tagged polymer in the eye was followed through the use of an ocular fluorimeter. The residence time of the cationic charged polymer was compared to a tagged control hydroxyethyl cellulose polymer placed in the contralateral eye.

| HEC RESIDENCE TIME (MIN.) | JR RESIDENCE TIME (MIN.) | LR RESIDENCE TIME (MIN.) | % INCREASE COMPARED TO CONTROL |
|---|---|---|---|
| 67 | | | |
| 37 | 107 | | 189 |
| 44 | 55 | | 25 |
| 59 | 91 | | 54 |
| 25 | | 37 | 48 |
| 47 | | 43 | −9 |
| 47 | | | 279 |
| 29 | 125 | | 331 |
| 75 | | 80 | 7 |
| 70 | | 59 | −16 |
| 76 | 157 | | 107 |
| 58 | 139 | | 140 |
| 37 | | 46 | 24 |
| 39 | | 75 | 27 |
| 52.1 | 112.3 | 56 | Average Residence Time |
| 0 | 141.0 | 13.7 | Average % Increase Relative to HEC |

The above residence times demonstrate the ability of an anionic therapeutic agent covalently bonded to a cationic polysaccharide polymer to be substantive to mucosal surfaces of the eye. The percentage increase in residence times of JR indicates that this composition was substantive to the eye. However, the LR polymer did not demonstrate the same degree of substantivity to the eye as represented in the lower percentage increase in comparison to the HEC, e.g., (48, −9, 7, −16, 24, 27) and the average residence time of 56, as compared to the average residence time for HEC of 52.1.

Without wishing to be bound to any particular theory, it is believed that the LR was less effective in being substantive to the eye due to the lower cationic substitution of the polymer. The JR polymer contains a higher level of cationic substitution than LR, 0.4 vs 0.2.

EXAMPLE 2

The forces bet

The forces between two mica sheets with or without absorbed polymer were measured using the method developed by Israelachvili et al., *J. Chem. Soc. Faraday Trans.* 1, 1978, 74, 975. The technique is further described by Patel and Tirrell in the *Minnesota Annual Review Physical Chemistry*, 1989, 40, 597. The described technique enables measurements of interaction forces between two surfaces ranging from several hundred nanometers to molecular contact. Forces can be measured to an accuracy of $10^{-4}$ dynes, and separations to less than 0.5 nanometers.

After mica was cleaved to give pieces of 1–5 micron thickness, they were glued to the silica disc elements and introduced into the apparatus. Initially, the surfaces were brought into contact in air and then in water to ensure the absence of any contamination in the system. The water was passed through a 0.22 micron Millipore filter before introduction to the system. All subsequent solutions were filtered in this way. After the water was drained from the system, a solution of 1000 parts per million (ppm) JR was prepared and introduced. The surfaces were kept far apart and the polymer was allowed to adsorb for 4 hours after which the force measurements were made. Several compressions and expansions were performed. The solution was then drained and water introduced. It was confirmed that there was negligible desorption caused by this water "washing". The water was then drained, and a 0.3 ppm solution of hyaluronic acid was introduced. The system was allowed to equilibrate for 2 hours, and force measurements were again made.

In FIG. 1 are shown the data for JR by itself. It is seen that in the first approach, repulsion begins at 1100 A and that the polymer can be squeezed down to about 90 A. The polymer is never completely squeezed from between the surfaces. Upon expansion, there is hysteresis indicating that the polymer has been irreversibly compressed onto the surface. In further compression-expansion cycles, the force profile follows that of the first expansion, and does not return to that observed in the original compression.

Figure 2:
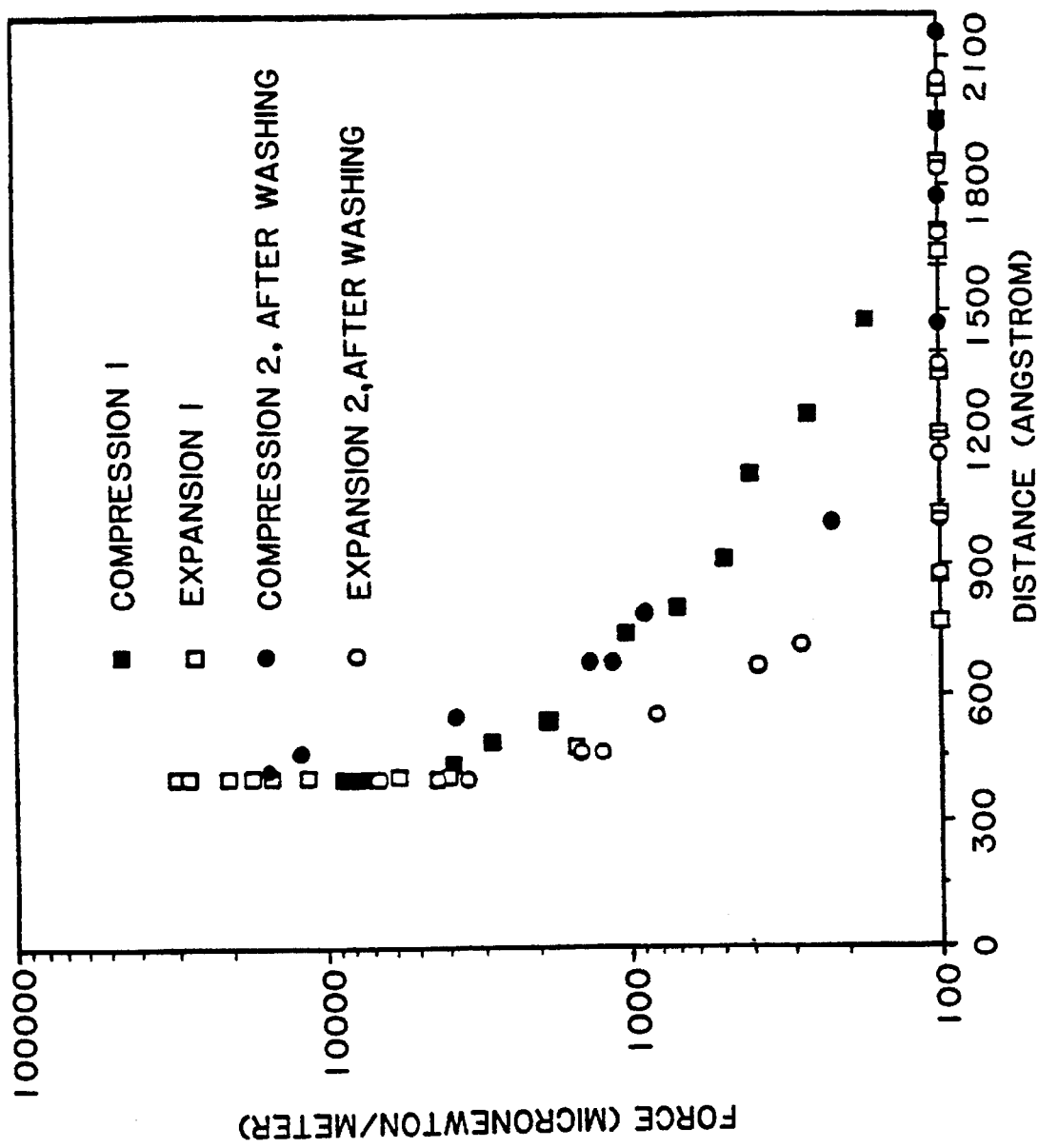
FIG. 2 is a force versus distance profile of an aqueous hyaluronic acid solution (0.3 parts per million) squeezed between two mica plates to which UCARE® Polymer JR 400 had been preabsorbed.

FIG. 2 demonstrates the force profiles for the JR/hyaluronic acid solution. It is seen that in the initial compression, repulsion begins at 1700 A. This is a much thicker polymer layer than observed for JR alone, indicating that the hyaluronic acid has been electrostatically bound to JR. The cationic/anionic polymer complex formed can only be squeezed down to about 400 A, even under high applied forces. This is in contrast to JR alone which can be squeezed down to 90 A and indicates very strong binding between the two polymeric materials.

The behavior that is observed in this experiment is direct evidence that the cationic polymer is responsible for binding the anionic therapeutic agent to the substrate. This increased thickness is also indication of enhanced substantivity of the cationic polysaccharide to the surface by the incorporation of the anionic therapeutic agent.

EXAMPLE 3

A dialyzed aqueous mixture of 0.5 weight percent fluorescein labeled JR and 0.05 weight percent hyaluronic acid was prepared in balanced salt solution to provide neutral pH and isotonicity for topical occular use. The solution remained clear and precipitate free. The solution was sterilized by filtration.

A 20 microliter drop of the JR/hyaluronic acid formulation was placed in the eye of a human subject. No signs of irritation were observed. Ocular fluorimetry of the tear film demonstrated significant substantivity with the fluorescein labeled JR.

Four other dialyzed aqueous mixtures of 0.5 wt % JR with different therapeutic agents (penicillin V, K salt, 0.2 wt %; methyl anthranilate, 0.2 wt %; salicylic acid, 0.2 wt %; and 2-anthramine, 0.2 wt %) were made as described above.

Quite surprisingly, the solutions containing the anionic therapeutic agents, i.e., penicillin V, methyl anthranilate and salicylic acid, remained clear and precipitate free whereas the cationic therapeutic agent, i.e., 2-anthramine, was cloudy. This finding was in complete contrast to what was expected, i.e., that two oppositely charged species would agglomerate and precipitate out of solution and two similarly charged species would repel each other and stay in solution.

An additional mixture was made with the methyl anthranilate at a concentration of 0.6 wt %. At this concentration, the solution was cloudy. Thus, it is preferred that the concentration of the anionic therapeutic agent be less than 0.6 wt % in salt solutions based on the weight of the water, cationic polymer, anionic therapeutic agent and salt.

EXAMPLE 4

A dialyzed aqueous 0.5 weight percent JR and 0.2 weight percent hyaluronic acid was prepared in balanced salt solution to provide neutral pH and isotonicity for topical occular use. A second solution was also prepared using 0.25 weight percent JR and 0.1 weight percent hylaluronic acid. The second solution was also a balanced salt solution suitable for opthalmic use. Both solutions were clear and free of precipitates.

A 50 microliter drop of the high concentration solution was placed in a human eye. The person reported that the solution was very comfortable in the eye and no irritation or foreign body sensation was reported.

We claim:

1. In a method for delivery of an anionic therapeutic agent to a mucosal surface, which method comprises providing a composition to said mucosal surface, said composition comprising:
   (a) water;
   (b) an effective amount of a cationic polysaccharide polymer to provide substantivity to the mucosal surface; and
   (c) an effective amount of an anionic therapeutic agent to provide delivery of the anionic therapeutic agent to the mucosal surface; The improvement wherein:
      (i) said cationic polvsaccharide comprises a quaternary-nitrogen radical substituted with members selected from the group consisting of alkyl and alkoxyalkyl radicals each containing up to 4 carbon atoms, said quaternary-nitrogen radical substituted on said polysaccharide at a degree of cationic substitution of greater than 0.1; and
      (ii) said composition comprises an effective amount of a salt to provide a clear solution of said composition.

2. The method of claim 1 wherein the mucosal surface is the eye.

3. The method of claim 1 wherein the cationic polysaccharide polymer is a cationic cellulosic.

4. The method of claim 3 wherein the anionic therapeutic agent is a glycosoaminoglycan.

5. The method of claim 1 wherein the anionic therapeutic agent is selected from the group consisting of hyaluronan, hyaluronic acid, hyaluronan derivatives, penicillins, salicylic acid, anthranilic acid, derivatives and salts thereof.

6. The method of claim 1 wherein the effective amount of the cationic polysaccharide is from about 0.0025 to 20.0 wt % based on the total weight of the solution.

7. The method of claim 1 wherein the effective amount of the anionic therapeutic agent is from about 0.0001 to 2.0 wt % based on the total weight of the solution.

8. The method of claim 1 wherein the substitution level of the quaternary nitrogen compound is from about 0.2 to 1.0 mole per mole of the polysaccharide.

9. The method of claim 1 wherein the relative weight ratio of the cationic polysaccharide polymer to anionic therapeutic agent is from about 1:1 to about 200:1.

10. The method of claim 11 wherein the solution has a viscosity of less than 50 centipoise.

11. In a composition for delivery of an anionic therapeutic agent to a mucosal surface, which composition comprises:
    (a) water;
    (b) an effective amount of a cationic polysaccharide polymer to provide substantivity to the mucosal surface; and
    (c) an effective amount of an anionic therapeutic agent to provide delivery of the anionic therapeutic agent to the mucosal surface; The improvement wherein:
       (i) said cationic polysaccharide comprises a quaternary-nitrogen radical substituted with members selected from the group consisting of alkyl and alkoxyalkyl radicals each containing up to 4 carbon atoms, said quaternary-nitrogen radical substituted on said polysaccharide at a degree of cationic substitution of greater than 0.1; and
       (ii) said composition comprises an effective amount of a salt to provide a clear solution of said composition.

12. The composition of claim 11 wherein the anionic therapeutic agent is selected from the group consisting of hyaluronan, hyaluronic acid, hyaluronan derivatives, penicillins, salicylic acid, anthranilic derivative acid and salts thereof.

13. The composition of claim 11 wherein the concentration of the anionic therapeutic agent is from about 0.001 to 0.6 wt % based on the total weight of the composition.

14. The composition of claim 11 wherein the polysaccharide is a cationic cellulosic.

15. A method for delivery of an anionic therapeutic agent to an eye which method comprises providing a composition to said eye said composition comprising:
    (a) water;
    (b) an effective amount of a cationic polysaccharide polymer having a quaternary-nitrogen radical substituted with members selected from the group consisting of alkyl and alkoxyalkyl radicals each containing up to 4 carbon atoms, said quaternary-nitrogen radical substituted on said polysaccharide at a degree of cationic substitution of greater than 0.1 and effective to provide substantivity to said eye;
    (c) an anionic therapeutic agent; and
    (d) an effective amount of a salt to provide a clear solution of said composition.

16. The method of claim 15 wherein the cationic polysaccharide polymer is a cationic cellulosic.

17. The method of claim 15 wherein the anionic therapeutic agent is selected from the group consisting of hyaluronan, hyaluronic acid, hyaluronan derivatives, penicillins, salicylic acid, anthranilic acid, derivatives and salts thereof.

* * * * *